Figure 1A:
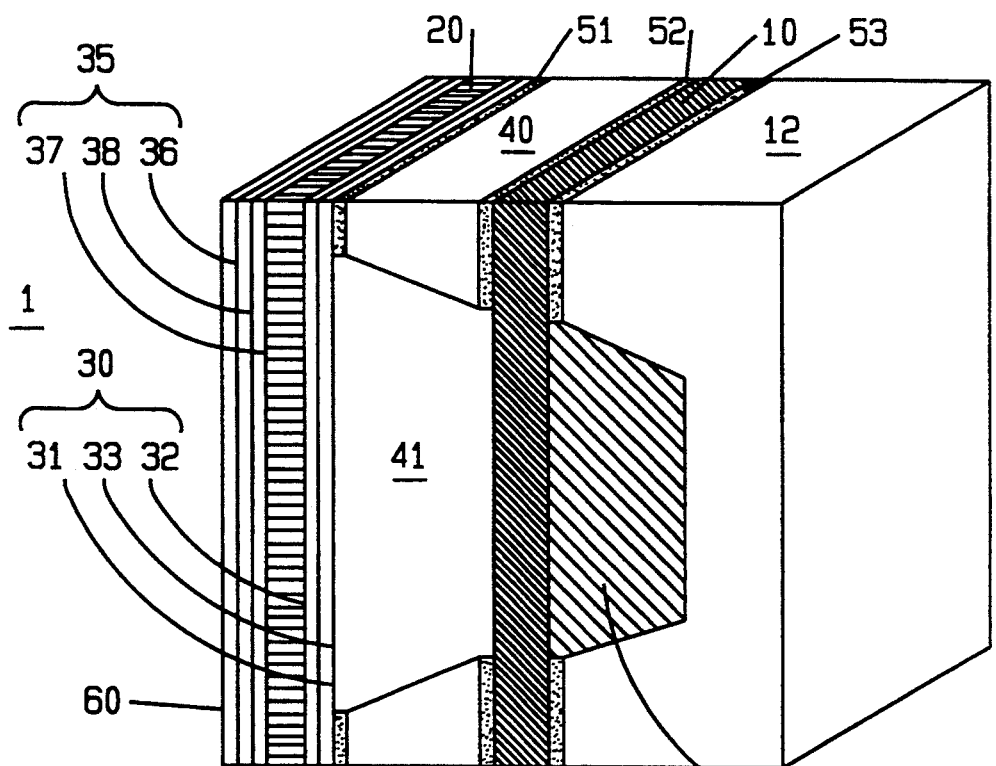

United States Patent [19]
Neftel

[11] Patent Number: 5,337,747
[45] Date of Patent: Aug. 16, 1994

[54] IMPLANTABLE DEVICE FOR ESTIMATING GLUCOSE LEVELS

[76] Inventor: Frédéric Neftel, 1, Rue des Escouffes, Paris, France, 75004

[21] Appl. No.: 1,433

[22] Filed: Jan. 7, 1993

Related U.S. Application Data

[63] Continuation of Ser. No. 687,916.

Foreign Application Priority Data

Oct. 6, 1989 [FR] France ............................ 8913069

[51] Int. Cl.⁵ .................................................. A61B 5/00
[52] U.S. Cl. ...................................... 128/635; 128/637; 128/748; 604/66
[58] Field of Search ................. 204/403, 415; 128/635, 128/632, 637, 746, 750; 604/65–67

[56] References Cited

U.S. PATENT DOCUMENTS

| | | | |
|---|---|---|---|
| 4,431,004 | 2/1984 | Bessman et al. | 204/403 |
| 4,538,616 | 9/1985 | Rogoff | 604/66 |
| 4,822,336 | 4/1989 | DeTraglic | 604/66 |
| 4,890,620 | 1/1990 | Gough | 204/403 |

*Primary Examiner*—William E. Kamm
*Assistant Examiner*—Robert L. Nasser, Jr.

[57] ABSTRACT

An implantable device which comprises two measurement chambers each of which comprises an internal measurement chamber insulated from its surroundings by a glucose-hemipermeable membrane for the first measurement chamber, and by a glucose-permeable membrane which is impermeable to molecules larger than glucose for the second measurement chamber, connected to a pressure sensor for each of the measurement chambers, and linked to an electronic system provided for informing the environment outside the organism of the value of the pressure measured in each of the two measurement chambers and, therefore, of the glucose level.

15 Claims, 2 Drawing Sheets

IMPLANTABLE DEVICE FOR ESTIMATING GLUCOSE LEVELS

This is a continuation of application Ser. No. 07/687,916, filed May 31, 1991, now abandoned.

The present invention relates to the field of medical devices and, more particularly, to an implantable device for obtaining a simple and an accurate estimation of the blood glucose level of an individual.

The problems associated with the determination of the glucose level in diabetics' blood are well known, in particular those arising from the burdensome and aggressive nature of the methods which are used. They may require, for example, that 2 to 3 times every day, a drop of blood be drawn from a fingertip and placed in a "glucometer" such a method being very fast and accurate, but leaving sequelae, which become important in the long run. Also, a subcutaneous electrode connected to the outside by electrical leads can be used, which can remain in place for 3 to 7 days, but which requires considerable precautions to maintain asepsis and causes permanent discomfort to the patient.

And yet, an accurate measure of the glucose level in the blood is indispensable for adjusting correctly the dose of insulin to be administered at each meal. Otherwise, the patient would expose himself to considerable risks. Among the short-term risks, one can mention hypoglycemia or hyperglycemia leading eventually to coma, and among the long-term risks, all the problems of peripheral arteriopathy (arteriosclerosis obliterans), which can lead to blindness or amputation of extremities. The diabetics, confronted with these grave problems, have learned to adjust the doses of insulin by repeatedly measuring the glucose level and strictly controlling their diet and their physical effort. One will appreciate the importance and the impact of the conditions under which these patients measure the glucose level in their blood.

The object of the invention is to provide a nonaggressive method for estimating accurately the glucose level in the blood of an individual, by means of a highly compact device, which is implanted, for example, in a subcutaneous region.

It is well known, that there is a very good correlation between the blood glucose level and the interstitial glucose level prevailing, for example, in the subcutaneous regions. In fact, glucose diffuses freely through the vessels into the interstitial regions.

It is also well known, that the major composition changes of the interstitial liquid involve changes in a limited number of substances, amongst which glucose. Of these substances with spatial dimensions of the same order as those of molecules of glucose (approximately 0.8 nm) glucose is the one which varies to the greatest extent. This is why a selective measure of the osmotic pressure due to molecules with spatial dimensions equalling those of glucose reflects relatively accurately the osmotic pressure of glucose in the considered region and, therefore, the blood glucose level. Naturally, this type of measure can be made in any compartment in glucosic equilibrium with the blood compartment (for example, the subcutaneous region or the peritoneal cavity).

Some authors have claimed they can determine the level of glucose by the sole measurement of the osmotic pressure exerted by the totality of the molecules having spatial dimensions exceeding those of glucose, this measurement being carried out by means of a glucosehemipermeable membrane. One can note in particular U.S. Pat. No. 4,538,616 to Robert Rogoff, which describes such a system. However, it should be noted that the variations which occur in the state of hydration of the patient or even more likely in some amino acids, to mention just a few examples, can cause considerable changes in the osmotic pressure of the individual and in the approach which is disclosed, be conducive to misinterpretations, the consequences of which can be extremely serious for the patient.

In its principle, the invention consists in measuring accurately inside an interstitial region, the absolute value—or the changes—of the osmotic pressure due to molecules with spatial dimensions equalling those of glucose, by means of highly compact implanted device. Such a measure can be made in any region or compartment in glucosic equilibrium with the vascular compartment. The osmotic pressure due to glucose and, consequently, the level of circulating glucose, can be derived from this measured value.

Numerous miniaturized devices for measuring pressure are already known, which are made of photolithographically machined silicon. A pressure sensor made according to such techniques could be used advantageously because of its very small final volume (a few $mm^2$ for a thickness less than one mm). In particular, the sensitivity characteristics which are attained are quite compatible with the pressure variations which are to be measured, and which amount to several millimeters of mercury.

Various types of membranes are further known, having accurately dimensioned perforations which allow the passage of water, ions, lactates, but not of glucose. Such membranes are said to be glucose-hemipermeable. The diameter of the perforations ranges in this case, from about 0.6 nm to about 0.74 nm.

Membranes are also known, which have perforations larger than the molecules of glucose, thereby allowing the passage of glucose. By choosing such a membrane with perforations having a diameter in the order of 0.9 nm, a membrane can be obtained which is said to be at the limit of permeability to glucose.

Biocompatible coatings are also known which are permeable to glucose and to numerous other molecules, but which are non permeable to cells. Such coatings, for example those made of polymers of perfluorosulfonic acid (Nafion ® from Du Pont de Nemours) have the advantage of not becoming obstructed after several years in an interstitial region and of not being rejected by the body.

Accordingly, such a coating can be used advantageously as a biocompatible protective membrane.

The invention consists in an assembly of two measuring chambers comprised of:
- on the one hand, a first chamber for measuring osmotic pressure which is directly in contact with a first pressure sensor and which is separated from the interstitial medium by a glucose-hemipermeable membrane, said membrane being separated from the interstitial medium by a protective biocompatible membrane;
- on the other hand, a second chamber for measuring osmotic pressure which is directly in contact with a second pressure sensor and which is separated from the interstitial medium by a membrane at the limit of permeability to glucose, said membrane being also separated from the interstitial medium by a biocompatible protective membrane.

The device according to the invention makes it possible to measure accurately an absolute osmotic pressure or differences in osmotic pressures corresponding to molecules of the same dimensions as glucose. A coupling of the two pressure sensors to an electronic system, permits the transmission of the measured values to a receiver located outside the body of the individual. Such an electronic system can be, in particular, a variable-frequency LC-type resonant passive system, responsive to a radiofrequency signal emitted from outside. In this case, the electronic system requires no power supply and can therefore remain implanted for a very long period of time. Such a resonant pressure sensor was developed by a Swedish research team from the Uppsala Institute of Technology for measuring intraocular pressure, and was presented at the "Transducer 89" Congress in Montreux, Switzerland, June 26th, 1989 (Ylbva Bäcklund, Lars Rosengren and Betril Hök, from the Uppsala Institute of Technology, and Björn Svedbergh from the Uppsala Institute of Ophthalmology). Such a resonant system is already currently used in the industry and was described for the first time by Collins in 1967.

Other objects and advantages of the present invention will become apparent from the following description and from the appended drawings, given for purposes of illustration and without any intent to be limiting.

FIGS. 1a & b are schematic drawings of one of the two measuring chambers forming the device, showing in crosssection the various components which form the chamber.

Figure 2B:
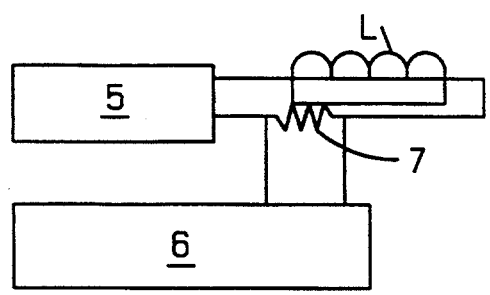
Figure 2A:
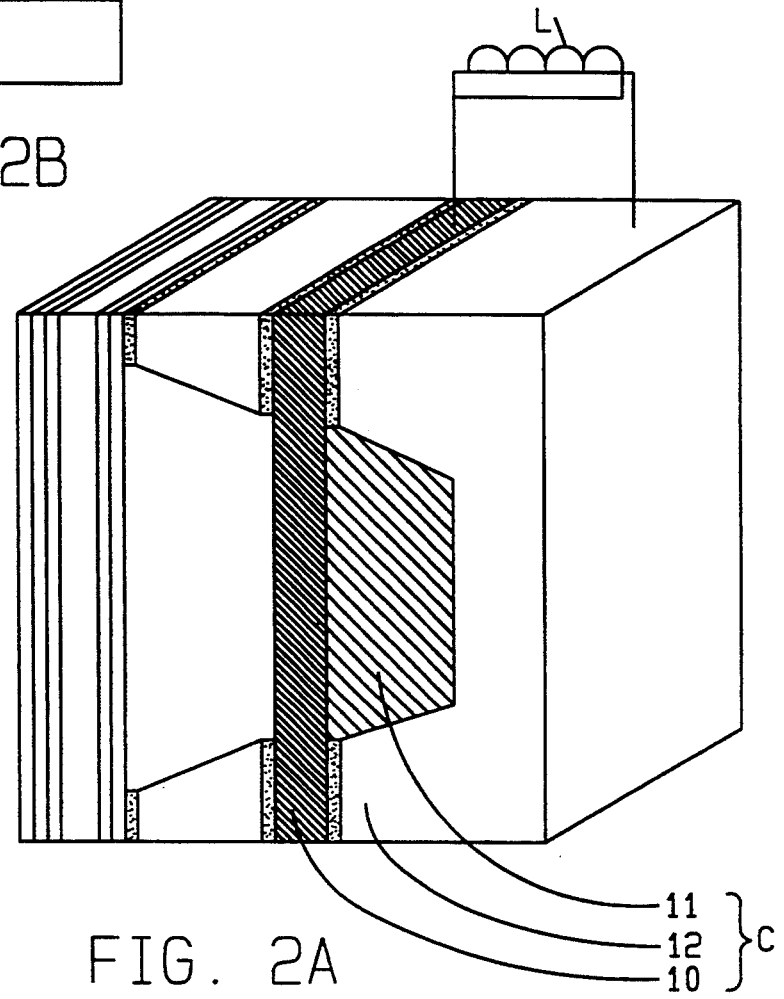
Figure 3:
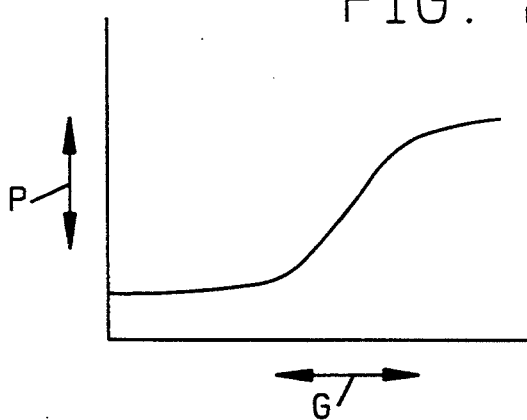

FIGS. 2a & b are schematic drawing of one of the two measuring chambers forming the device in accordance with the present invention, this FIGURE showing electronic elements of this chamber and the corresponding external emitter. FIG. 3 shows a typical resonance frequency curve which can be obtained with the type of pressure sensor described for each one of the two measuring chambers of the device.

It should be noted, that for the sake of clarity, the relative thickness and dimensions of the various components of the device are not respected.

Figure 1B:
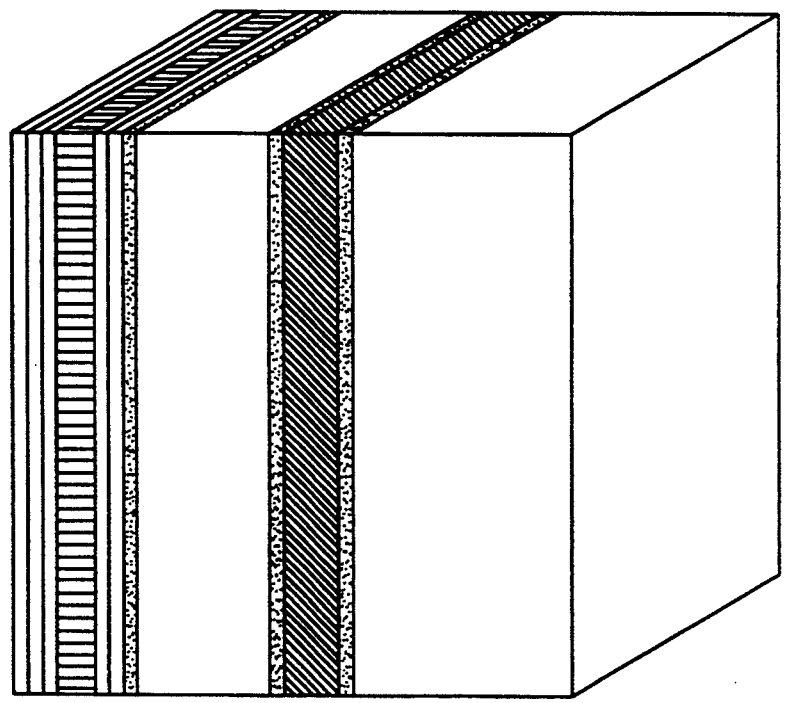

Referring to FIG. 1, one can describe the various components which compose one of the two measuring chambers forming the device according to the invention, placed in an environment 1, in which the osmotic pressure due to molecules of the same dimensions as glucose, is to be measured. The two measuring chambers are equivalent insofar as their operations are concerned and we shall therefore limit our description to the first one, which differs from the second one only by the properties of the hemipermeable membrane which is used. For this first measuring chamber, there is shown in FIG. 1 two parts A and B providing an exploded view of this measuring chamber along a sagittal sectional plane taken through the middle thereof. The membrane 20 is of a glucose-hemipermeable type, i. e. permeable to water and to molecules smaller than glucose, but non permeable to glucose. The thickness of this membrane will be chosen according to its nature. The cavity 41, machined by a photolithographic technique (using KOH as etching agent) in a layer of silicon 40 about 30 $\mu$m thick, provides the internal chamber for measuring the osmotic pressure. The pressure sensor consists of the membrane 10 and of the layer 12, as well as of the cavity 11, the membrane 10 being directly exposed to the internal measuring chamber 41. The membrane 10 is a p+ doped silicon membrane about 20 $\mu$m thick and is oxidized on the one hand, in the peripheral area 53 and on the other hand, in the area 52, in order to make possible its hot bonding (at 1000° C.), respectively to the layer 12 and to the layer 40. The layer 53 acts also as an insulant between the membrane 10 and the layer 12, to provide a variable capacitor. The layer 12, which is approximately 60 $\mu$m thick, is hollowed in its middle by the application of a photolithographic technique (using KOH as etching agent), to form a cavity 11 about 20 $\mu$m deep and facing the layer 10.

This cavity 11 must be perfectly well sealed in order to ensure a satisfactory accuracy and avoid any significant drift of the pressure sensor in the course of time.

The pressure sensor functions then as a variable capacitor, the capacitance of which varies as a function of the deformation of the membrane 10, under the effect of the pressure prevailing in the chamber 41.

In order to optimize the yield of the pressure measures obtained from the membrane 10 of the pressure sensor, the membrane 20 is stiffened by means of a layer 30, made for example from silicon according to the procedure developed by Gjermund Kittilsland and Göran Stemme (Depart. of Solid State Electronics, Chalmer Univ. of Technology, Gothenburg, Sweden) and presented at the "Transducer 89" Congress in Montreux, Switzerland, on June 26th, 1989. This type of layer offers the advantage that it can be made from silicon to any desired thickness and accordingly, to exhibit a high coefficient of rigidity, and that it has pores of a small diameter. This type of layer is prepared by hot bonding together two perforated silicon membranes 31 and 32, the perforations of which do not coincide, via a thin silicon dioxide layer 33, provided on the two surfaces facing each other and the thickness of which is perfectly well defined. This layer 30 is oxidized on the periphery 51 on the side facing the layer 40, in order to permit its hot bonding thereto. A layer of the same nature 35 (made of the perforated membranes 36 and 37, as well as of a thin layer of silicon dioxide 38) can also be provided on the other side of the membrane 20.

In order to avoid obstructing, on the one hand, the pores of the stiffening layer 30 or 35 and, on the other hand, those of the membrane 20, a biocompatible protective layer 60 is applied to cover the totality of the device. In particular, such a layer must be permeable to molecules smaller than glucose, as well as to glucose. It can, for example, consists of a layer of a polymer of perfluorosulfonic acid, the long-term stability of which is excellent in subcutaneous tissue. The protection offered by this layer is directed more particularly against cells and deposits, such as those of fibrin.

The second measuring chamber forming the device is identical to the first measuring chamber described above, with the only difference that its membrane 20 is selected so as to be at the limit of permeability for glucose, i.e. it allows the passage of glucose but not of molecules larger than glucose.

Finally, the size of such a device comprising two measuring chambers of the type described is totally compatible with its implantation, since its thickness amounts to about 300 $\mu$m and its sides to about 2 mm.

FIG. 2 illustrates the electronic operations of each one of the measuring chambers of the device, which rely on the use of a LC-type resonant passive circuit.

The capacitor C is provided by the pressure sensor comprised of the layers 10 and 12 isolated from each other by the silicon dioxide layer 53. Any movement of the membrane 10 under the effect of a change of pressure inside chamber 41 results in a change of the value of C. This capacitor is mounted in parallel with a self-inducting coil L and, therefore, any change in C results automatically in a change in the resonance frequency, in accordance with the relation $f = \frac{1}{2}\pi(LC)^{\frac{1}{2}}$. This resonance frequency is measured at a distance by a magnetically coupled oscillator, which converts the measured value into an osmotic pressure value in the cavity 41 and the difference between the two values obtained within the two measuring chambers into the osmotic pressure due to molecules the spatial dimensions of which are identical to those of glucose; by deduction and comparison with a reference value, a glucose level is obtained. This external electronic assembly comprises consequently for each one of the measuring chambers an assembly comprised of a variable frequency oscillator 5, a self-inducting coil L' and a resonance detector 6 at the terminals of a resistor 7, the resonance characteristics of each one of the measuring chambers being different, so that they may be analysed from outside without interference.

For the glucose levels currently found in diabetics and which can range from 0.6 g/l to 3 g/l, Van't Hoff's relation for calculating the resulting osmotic pressures is as follows:

$$\cap = RTc/M$$

where $\cap$ = osmotic pressure, R = gas constant, T = absolute temperature in °K, c = concentration in weight, M = molar mass, and the corresponding osmotic pressures range from 60 to 300 mm Hg. In order to ensure an accuracy of several percent for the measures, the pressure sensor must have a sensitivity in the order of several mm Hg.

In order to carry out the measures under optimal conditions which take into account physiological changes and the characteristics of the pressure sensor, one can define a concentration of macromolecules to be placed inside the cavity 41 for measuring the osmotic pressure. In order to achieve a broad measuring range and to ensure a high level of accuracy, several individual measuring chambers can be used in parallel to simulate a single measuring chamber of the device, each one of these individual multiple measuring chambers receiving within their internal measuring chamber a different concentration of macromolecules. Quite obviously, the resonance frequency of each of the sensors is selected to be different, so that each measuring sensor can be analysed from outside without interference.

FIG. 3 shows a typical resonance frequency curve as it can be obtained with the above-described pressure sensor. It can be seen, that the highest sensitivity is achieved for a certain pressure range P which should be adapted to the glucose level range G useful for diabetics.

In order to limit the interaction between the biocompatible membrane and the surrounding medium, and thus to increase the useful life of the device, one can select a particular position for the implant. Thus, the peritoneal cavity and the subcutaneous interstitial tissue are regions which are more favorable from this standpoint. For example, the subcutaneous abdominal region is particularly well suited, since the device can be implanted in this region easily and safely.

Naturally, in order to increase the reliability of the measures, several devices can be implanted in the same place or in different places, the result which is obtained being considered as valid only when the values obtained from the various devices are in good agreement. In this case also, the resonance frequencies of each one of the individual sensors will be selected so as not to create interference.

It should also be noted, that the two measuring chambers described for forming the device can also be engineered advantageously within the same housing, or even be formed by a photolithographic process on the same substrate.

It is also obvious, that depending on the type of hemipermeable membrane which is selected and also on its performance in prolonged use, it may be necessary to measure osmotic pressure changes rather than absolute osmotic pressures. Actually, only membranes which remain totally non permeable to glucose and are exactly at the limit of non permeability to glucose in the long term can provide an absolute value for the osmotic pressure according to the method described. In the case of membranes which are more or less of an obstacle to the passage of glucose (in accordance to Renkin's adapted diffusion laws, as a function of the diameter of the membrane pores) a measure can only be a osmotic pressure difference, with respect to a reference value which is variable. Accordingly, depending on the rate of glucose passage for each one of the membranes, one can either be satisfied with the specific characteristics of these membranes or carry out an accurate measurement of the reference value at regular intervals of time, for example by drawing blood.

Another advantage of the invention is that the informations obtained by the device can be fed directly to an insulin micropump, to enable an automatic adjustment of the insulin doses to be administered to the patient. Such a comprehensive system constitutes a truly artificial pancreas.

I claim:

1. An implantable device for estimating the glucose level by measuring the osmotic pressure due to glucose, characterized in that it comprises:

a first measuring chamber insulated from the surrounding medium by a first glucose-hemipermeable membrane, said first chamber cooperating with a first pressure sensor, which in turn is connected to an electronic system for transmitting information pertaining to the value of a measured pressure, a second measuring chamber insulated from the surrounding medium by a second membrane permeable to glucose and non-permeable to molecules larger than glucose, this second chamber cooperating with a second pressure sensor, which in turn is connected to an electronic system for transmitting information pertaining to the value of the measured pressure, and means associated with said first and second pressure sensors for providing through the difference between the measured pressures, an accurate estimation of the osmotic pressure due solely to glucose and, consequently, of the glucose level.

2. A device according to claim 1, characterized in that the first membrane is stiffened by a third perforated membrane of a low elasticity, in order to reduce the dampening of the pressure prevailing inside the first measuring chamber by the first membrane and, therefore, to optimize the yield of the first pressure sensor.

3. A device according to claim 2, characterized in that the third perforated membrane is produced by photolithographic techniques.

4. A device according to claim 1, characterized in that the first pressure sensor is made of photolithographically machined silicon.

5. A device according to claim 1, characterized in that the electronic system connected to the first pressure sensor is a LC-type resonant passive system, the resonance frequency of which varies as a function of the pressure which is measured, the value of this pressure being determined by a magnetically coupled variable oscillator.

6. A device according to claim 1, characterized in that each of the measuring chambers contains macromolecules, the concentration of which is selected according to the values of the osmotic pressures which are to be measured and to the optimal operational range of the first and second pressure sensors.

7. A device according to claim 1, characterized in that the first membrane is in turn protected from the outside medium in which the device is implanted by a fourth biocompatible membrane which is non-permeable to cells but permeable at least to glucose and water.

8. A device according to claim 1, characterized in that the device is adapted to be implanted into subcutaneous tissue.

9. A device according to claim 1, characterized in that it includes means for automatically transmitting the results of the measurements to an insulin micropump to enable the administration of a desired amount of insulin so that the assembly functions as a substitute for the normal pancreatic functions of the patient.

10. A device according to claim 1, characterized in that the means for providing an estimation of glucose levels includes means to take into account variations of such levels over time, by comparison with a data base established for a value or for known variations of the blood glucose level, this data base optionally being re-established at regular intervals of time of operation, depending on the nature of the selected hemi-permeable membrane or on the patient.

11. An implantable device for estimating the glucose level by measuring the osmotic pressure due to glucose, characterized in that it comprises:
- a first measuring chamber insulated from the surrounding medium by a first glucose-hemipermeable membrane, said first chamber cooperating with a first pressure sensor, which is turn is connected to an electronic system for transmitting information pertaining to the value of a measured pressure,
- a second measuring chamber insulated from the surrounding medium by a second membrane permeable to glucose and non-permeable to molecules larger than glucose, this second chamber cooperating with a second pressure sensor, which in turn is connected to an electronic system for transmitting information pertaining to the value of a measured pressure, and
- means associated with said first and second pressure sensors for providing through the difference between the measured pressures, an accurate estimation of the osmotic pressure due solely to glucose and, consequently, of the glucose level,
- wherein the first and second membranes are each stiffened by a third perforated membrane of low elasticity, and each of the measuring chambers contains macromolecules, the concentration of which is selected according to the values of the osmotic pressures which are to be measured and to the optimal operational range of the first and second pressure sensors.

12. A device according to claim 11, characterized in that the means for providing an estimation of glucose levels includes means to take into account variations of such levels over time, by comparison with a data base established for a value or for known variations of the blood glucose level, this data base optionally being re-established at regular intervals of time of operation, depending on the nature of the selected hemipermeable membrane or on the patient.

13. A device according to claim 11, characterized in that the electronic system connected to the first and second pressure sensors is a LC-type resonant passive system, the resonance frequency of which varies as a function of the pressure which is measured, the value of this pressure being determined by a magnetically coupled variable oscillator.

14. A device according to claim 11, characterized in that the first and second pressure sensors are each made of photolithographically machined silicon.

15. An implantable device for estimating the glucose level by measuring the osmotic pressure due to glucose, characterized in that it comprises:
- a first measuring chamber insulated from the surrounding medium by a first glucose-hemipermeable membrane, said first chamber cooperating with a first pressure sensor, which in turn is connected to an electronic system for transmitting information pertaining to the value of a measured pressure,
- a second measuring chamber insulated from the surrounding medium by a second membrane permeable to glucose and non-permeable to molecules larger than glucose, this second chamber cooperating with a second pressure sensor, which in turn is connected to an electronic system for transmitting information pertaining to the value of a measured pressure, and
- means associated with said first and second pressure sensors for providing through the difference between the measured pressures, an accurate estimation of the osmotic pressure due solely to glucose and, consequently, of the glucose level,
- wherein the first and second membranes are each stiffened by a third perforated membrane of low elasticity, and each of the measuring chambers contains macromolecules, the concentration of which is selected according to the values of the osmotic pressures which are to be measured and to the optimal operational range of the first and second pressure sensors,
- wherein the electronic system connected to the first and second pressure sensors is a LC-type resonant passive system, the resonance frequency of which varies as a function of the pressure which is measured, the value of this pressure being determined by a magnetically coupled variable oscillator, and each of the first and second pressure sensors is made of photolithographically machined silicon.

* * * * *